(12) United States Patent
Passaro

(10) Patent No.: US 7,161,015 B1
(45) Date of Patent: Jan. 9, 2007

(54) METHOD OF MAKING 2-FURYLALKYLKETONES

(75) Inventor: Linda Passaro, New Fairfield, CT (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 11/223,244

(22) Filed: Sep. 8, 2005

(51) Int. Cl.
*C07D 307/46* (2006.01)

(52) U.S. Cl. .................................... 549/483

(58) Field of Classification Search ............. 549/483
See application file for complete search history.

(56) References Cited

U.S. PATENT DOCUMENTS

| | | | |
|---|---|---|---|
| 4,254,043 A | | 3/1981 | Kuta |
| 5,259,701 A | | 11/1993 | Gerhart et al. |
| 6,642,237 B1 * | | 11/2003 | Tata et al. ............. 514/252.02 |

OTHER PUBLICATIONS

Nahm et al, Tet. Letters, vol. 22, No. 39, p. 3815-3818 (1981).*
Passaro et al., U.S. Appl. No. 10/979,842, filed Nov. 2, 2004.
Singh et al., "The Growing Synthetic Utility of Weinreb's Amide" *J. Prakt. Chem.*, 342(4), 340-347 (2000).
Nahm et al., "*M*-Methoxy-*N*-methylamides as Effective Acylating Agents" *Tetrahededron Lett.*, 22(39), 3815-3818 (1981).
Miyakoshi et al., "Synthesis of 3-Alkylcatechis via Intramolecular Cyclization" *Synth.-Stuttgart*, 5, 407-410 (1990).
Corey et al., "Oxidative Hydrolysis of 1,3-Dithiane Derivatives to Carbonyl Compounds Using N-Halosuccinimide Reagents" *J. Org. Chem.*, 36(23), 3553-3560 (1971).
Gilman et al., "Super-Aromatic Properties of Furan. II. The Friedel-Crafts Reaction" *J. Am. Chem. Soc.*, 55(10), 4197-4205 (1933).
Goossen et al., "Palladium-Catalyzed Synthesis of Aryl Ketones from Boronic Acids and Carboxylic Acids Activated in situ by Pivalic Anhydride" *Eur. J. Org. Chem.*, 19, 3254-3267 (2002).
Goossen et al., "Palladium-Catalyzed Synthesis of Aryl Ketones from Boronic Acids and Carboxylic Acids or Anhydrides" *Angew. Chem. Int. Ed.*, 40(18), 3458-3460 (2001).

Jun et al., "Hydroacylation of 1-Alkene with Heteroaromatic Aldhyde by Rh(I) and Additives" *Tetrahedron Lett.*, 38(38), 6673-6676 (1997).
Komoto et al., "Catalytic Friedel-Crafts Acylation of Heteroaromatics" *Top. in Catal.*, 19(1), 43-47 (2002).
Passaro et al., "Synthesis of 2-Furyl-n-pentylketone, Antifouling Agent of the Future" ACS National Meeting (poster presentation), Anaheim, CA (Mar. 31, 2004).
U.S. Appl. No. 10/979,842, Passaro et al.
Corey et al, "Oxidative Hydrolysis of 1,3-Dithiane Derivatives to Carbonyl Compounds Using N-Halosuccinimide Reagents", Journal of Organic Chemistry, vol. 36, No. 23.
Gilman et al, "Super-Aromatic Properties of Furan II the Friedel-Crafts Reaction", Chemical Laboratory of Iowa State College, pp. 4197-4205, Oct. 1933.
Gooben et al, "Palladium-Catalyzed Synthesis of Aryl Ketones from Boronic Acids and Carboxylic Acids or Anhydrides",Angwe. Chem. Int. ED., vol. 40, No. 18, pp. 3458-3460, 2001.
Jun et al, "Hydroacylation of 1-Alkene with Heteroaromatic Aidehyde by Rh (1) and Additives", Tetrahedron Letters, vol. 38, No. 38, pp. 6673-6676, 1997.
Kobayashi et al, "Catalytic Friedel-Crafts Acylation of Heteroaromatics", Topics in Catalysis, vol. 19, No. 1, pp. 43-47, Mar. 2002.
Passaro et al, "Synthesis of 2-Furyl-n-Pentylketone, Antifouling Agent of the Furture", poster Presentation ACS National Meeting Anaheim, CA, Mar. 31, 2004.
Passaro et al, "Synthesis of 2-Furyl-n-pentylketone, Antifouling Agent of the Future"Center for Bio/Molecular Science and Engineering, Naval Research Laboratory, Washington.

* cited by examiner

*Primary Examiner*—Bernard Dentz
(74) *Attorney, Agent, or Firm*—John J. Karasek; Joseph T. Grunkemeyer

(57) ABSTRACT

A method of making a compound by: providing a furyl compound being 2-furoyl chloride or corresponding carboxylic acid, amide, ester, anhydride, or lactone; reacting the furyl compound with $CH_3O(CH_3)NH \cdot HCl$ to form an amide; reacting the amide with an alkane Grignard reagent or alkyllithium to form a chelated intermediate; and reacting the chelated intermediate with an aqueous acid to form a (2-furyl)-alkylketone.

9 Claims, No Drawings

METHOD OF MAKING 2-FURYLALKYLKETONES

BACKGROUND OF THE INVENTION

1. Field of the Invention

The invention relates to a process for the synthesis of 2-furylketones.

2. Description of the Related Art

Biological fouling, or biofouling, is defined as the unwanted buildup of microorganisms, plants, and animals on artificial surfaces. Marine biofouling is the undesirable accumulation of organisms on any artificial surface that is submerged in seawater, such as ship hulls, seaside piers, sea defenses, or any other surface that is continuously in contact with seawater. Biofouling of naval vessels causes an increase in surface roughness and higher frictional resistance. A slime layer as little as 1 mm in thickness can result in a 15% decline in ship speed (hydrodynamic drag). Increased drag of a vessel will result in higher operational costs, such as increased fuel consumption and decreased maneuverability.

Current antifoulant technologies have been found to be both harmful to marine life and to the environment. Presently, the most popular antifouling agents used in marine coatings worldwide are organotin compounds, namely tributyltin oxide (TBTO). Environmental concerns like these have pushed the EPA to investigate the effects of organotin antifoulants and as a result the International Maritime Organization (IMO) in October 2001 banned their use in marine paints as of Jan. 1, 2003. As a result, there is now an urgent need for new antifoulant technology that both effectively prevents organism growth and is environmentally friendly.

Naturally occurring antifoulant compounds are only available in limited amounts and often their structural complexity makes synthetic production in large quantities difficult. One analog of a naturally occurring antimicrobial agent, 2-furyl-n-pentylketone, has been a popular synthetic target. The majority of past synthetic strategies have involved Friedel-Crafts acylation chemistry and often resulted in poor yields and were rarely applied to large-scale preparations and/or involved the use of complex, expensive reagents. The various Friedel-Crafts acylation methods used to prepare 2-furyl-n-pentylketone have employed furan and an acid chloride or anhydride with a range of acid catalysts. Other groups have prepared 2-furyl-n-pentylketone by way of a facilitated acylation reaction between boronic acids and anhydrides in the presence of a palladium catalyst. Some groups have employed oxidative strategies of an α-hydroxyl furan that have proven difficult to carry out and the resulting ketone products often required chromatographic purification, which is troublesome for larger scale preparations. Alternative methods employed to prepare 2-furyl-n-pentylketone have involved an alkylation scheme usually involving either an acid chloride or furfural with the appropriate Grignard reagent. Alkylation in the case of furfural then required oxidation to afford the desired ketone product. Alternatively, 2-furyl-n-pentylketone may be prepared by way of the hydroacylation of 1-pentene with furfural in the presence of cocatalyst Wilkinson complex and 2-amino-3-picoline.

SUMMARY OF THE INVENTION

The invention comprises a method of making a compound comprising: providing 2-furoyl chloride or corresponding carboxylic acid, amide, ester, anhydride, or lactone; reacting the 2-furoyl chloride with $CH_3O(CH_3)NH\cdot HCl$ to form an amide; reacting the amide with an alkane Grignard reagent or alkyllithium to form a chelated intermediate; and reacting the chelated intermediate with an aqueous acid to form a (2-furyl)-alkylketone.

DETAILED DESCRIPTION OF EXAMPLE EMBODIMENTS

In the following description, for purposes of explanation and not limitation, specific details are set forth in order to provide a thorough understanding of the present invention. However, it will be apparent to one skilled in the art that the present invention may be practiced in other embodiments that depart from these specific details. In other instances, detailed descriptions of well-known methods and devices are omitted so as to not obscure the description of the present invention with unnecessary detail.

A process is disclosed wherein 2-furyl-alkylketones are prepared using Weinreb amide chemistry (Nahm et al., "N-methoxy-n-methylamides as effective acylating agents," Tetrahedron Lett., 22(39), 3815 (1981)). These highly applicable reaction intermediates may be used in the preparation of functionalized ketones via coupling with a variety of organometallic reagents. Conversion of 2-furoyl chloride into the corresponding Weinreb amide offers a stable intermediate that can easily be alkylated and reacted with the appropriate organometallic reagent of varying chain length and functionality to afford the desired corresponding 2-furyl-alkylketones.

The process is a two-step sequence in which the first involves the preparation of the Weinreb amide derivative of 2-furoyl chloride. The Weinreb amide could also alternatively be prepared from the corresponding carboxylic acid, amide, ester, anhydride, or lactone if the acid chloride is not available or easily prepared as long as the acid or acid derivative is sufficiently activated. Possible coupling agents include, but are not limited to, oxalyl chloride, 1,1'-carbonyldiimidazole, 2-halo-1-methylpyridinium salts, O-(benzotriazol-1-yl)-1,1,3,3-tetramethyluronium hexafluorophosphate, BOP (benzotriazol-1-yloxytris[dimethylamino]-phosphonium hexafluorophosphate), DCC (dicyclohexylcarbodiimide), S,S-di(2-pyridyl) dithiocarbonate, triphenylphosphine/carbon tetrabromide, and dimethylaluminum chloride. For example, a chloroform solution of 2-furoyl chloride is cooled to 0° C. and mixed with 1.10 equivalents of N,O-dimethylhydroxylamine hydrochloride followed by portion-wise addition of two equivalents of pyridine. Methylene chloride could also be used in the preparation of the Weinreb amide as opposed to chloroform. The mixture is allowed to stir for 15 minutes then allowed to warm to rt overnight to afford the Weinreb amide. The resulting amide is then dissolved in anhydrous diethyl ether or anhydrous tetrahydrofuran and is reacted with a slight excess of the appropriate, organometallic reagent at 0° C. The mixture is stirred for three hours further and worked up in the usual way to give crude furyl ketone. The crude residue is then distilled under vacuum to yield the desired furyl ketone.

The process allows for the simple preparation of large amounts of material with inexpensive reagents. The procedures may be applicable to large-scale preparations, may be easily carried out, and the necessary reagents may be inexpensive.

The synthetic strategy can offer yields in excess of 90%. This strategy may be easily scaled up and, due to the limited number of steps necessary and the high yield, is economical to produce. The present synthetic strategy can utilize a reasonable set of precursor reactants and can result in a high yield of product that may be easily cleaned up by simply using a polar and non-polar solvent pair and recovering the product from the hydrocarbon phase at yields exceeding 90%. Examples include, but are not limited to, the preparation of analogs where R is between 7 and 13, and may or may not be terminated with a protected hydroxyl or tertiary amine group to allow the compound to be bound at a surface.

In the first step of the process, a 2-furoyl chloride is reacted with $CH_3O(CH_3)NH \cdot HCl$ to form an amine as shown in Eq. (1). $R^1$, $R^2$, and $R^3$ can be hydrogen or any other groups. It is to be understood that in all cases, the mention of a reactant may refer to a single reactant or to a combination or mixture of more than one such reactant. Suitable solvents for the reaction include, but are not limited to, trichloromethane, methylene chloride, and pyridine.

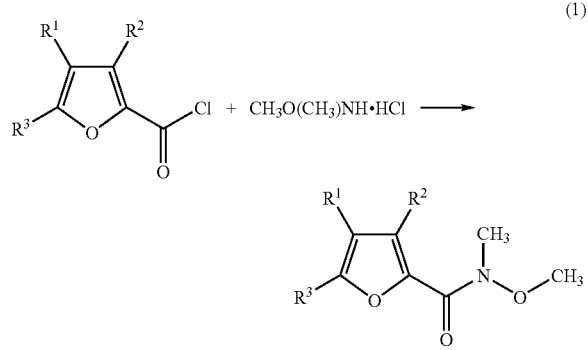

(1)

In the next step, the amine is reacted with an alkane Grignard reagent or alkyllithium to form an intermediate as shown in Eq. (2). These reactions are well known as to the reaction conditions and reagents that may be used. The R group may be an alkyl group and may be of lengths from $C_2$ to $C_{14}$, including branched and unbranched alkyl systems. The Grignard reagent may be, but is not limited to, a chloride or a bromide. Suitable solvents for the reaction include, but are not limited to, diethylether and tetrahydrofuran.

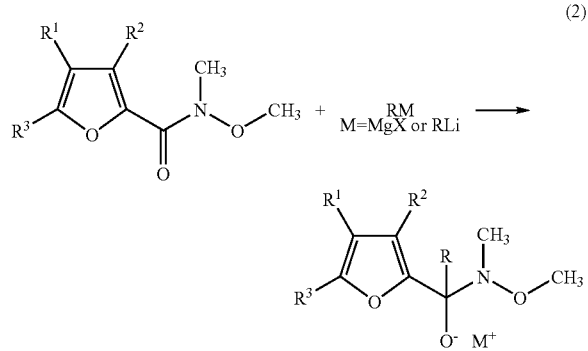

(2)

In the last step, the chelated intermediate is reacted with an aqueous acid to form a (2-furyl)-alkylketone as shown in Eq. (3). The final product may be purified by distillation and/or solvent extraction methods.

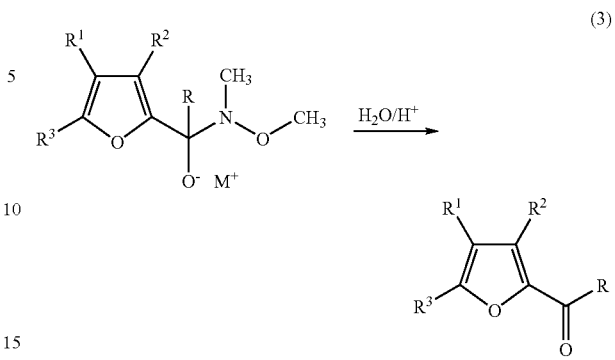

(3)

Having described the invention, the following examples are given to illustrate specific applications of the invention. These specific examples are not intended to limit the scope of the invention described in this application.

General—All bps are uncorrected. Thin-layer chromatography was carried out using Macherey-Nagel silica gel plates. NMR spectra ($^1$H and $^{13}$C) were obtained using a Bruker Avance at 400 MHz with CDCl3 as solvent. GC/FID sample analysis was carried out on a HP 6890 instrument equipped with a 30 m DB-5 column. Samples were heated from 50° C. (1 min.) to 280° C. (10 min) at a rate of 8°/min. All synthetic procedures were carried out with oven-dried glassware under a $N_2(g)$ atmosphere. Solvents were evaporated using a Buchi R-124 rotary evaporator unless otherwise indicated. All starting materials and reagents were obtained from Aldrich.

EXAMPLE 1

Preparation of N-Methoxy-N-methyl-2-furamide—2-Furoyl chloride (40 mL, 0.406 mol) was dissolved in 800 mL of EtOH free $CHCl_3$ (washed with $H_2O$ (3×) then dried ($Na_2SO_4$)) with N,O-dimethylhydroxylamine hydrochloride (43.6 g, 0.446 mol, 1.10 eq) and cooled to 0° C. Pyridine (66 mL, 0.816 mol, 2.0 eq) was added portion-wise and the mixture was stirred (15 min.) then warmed to rt overnight. The reaction mixture was then evaporated and the residue was partitioned between $Et_2O$ (400 mL) and brine (400 mL) then separated. The aqueous layer was extracted with $Et_2O$ (1×) and the combined organics are dried ($Na_2SO_4$), filtered, and evaporated to afford crude amide (54.8 g, 0.353 mol, Yld. 87.2%) that was taken on to the next step without further purification. $^1$H NMR: δ 7.54 (dd, 1H, $^3J_{H,H}$=1.7 Hz, $^4J_{H,H}$=0.70 Hz, H-2), 7.10 (dd, 1H, $^J_{H,H}$=3.5 Hz, $^4J_{H,H}$=0.70 Hz, H-4), 6.46 (dd, 1H, $^3J_{H,H}$=1.7 Hz, $^3J_{H,H}$=3.5 Hz, H-3), 3.71 (s, 3H, N—OCH$_3$), 3.30 (s, 3H, N—CH$_3$). $^{13}$C NMR: δ 159.1, 145.6, 145.2, 117.4, 111.6, 61.3, 33.1.

EXAMPLE 2

Preparation of 2-Furyl-n-pentylketone (R=n-$C_5H_{11}$)—Magnesium turnings (1.50 g, 62.5 mmol) were covered with anhydrous $Et_2O$ (20 mL) and a solution of 1-bromopentane (2.0 mL, 16.2 mmol) in anhydrous $Et_2O$ (16 mL) was added in small aliquots until the reaction begins. The remaining bromopentane solution was added dropwise, then heated to reflux (1 hour), allowed to cool to rt and then added to a cooled solution of the Weinreb amide (1.65 g, 10.6 mmol in 20 mL anhydrous $Et_2O$, 0° C.) via cannula. The resulting slurry was stirred (3 h) and then quenched with equal amounts of 1 N HCl and H$_2$O. After warming to rt the mixture was separated and the aqueous layer was extracted with Et$_2$O (2×). The combined organics were washed with sat'd. NaHCO$_3$, brine, dried (Na$_2$SO$_4$), filtered, and evaporated to yield crude furyl ketone, which was distilled under vacuum (b.p. 73–74° C., 0.2 mm Hg) to give pure furyl ketone (1.45 g, 8.72 mmol, Yld. 82.3%). $^1$H NMR: δ 7.57 (dd, 1H, $^3J_{H,H}$=1.6 Hz, $^4J_{H,H}$=0.76 Hz, H-2), 7.17 (dd, 1H, $^3J_{H,H}$=3.5 Hz, $^4J_{H,H}$=0.74 Hz, H-4), 6.52 (dd, 1H, $^3J_{H,H}$=1.6 Hz, $^3J_{H,H}$=3.5 Hz, H-3), 2.80 (t, 2H, $^3J_{H,H}$=7.4 Hz, H-7), 1.71 (quintet, 2H, $^3J_{H,H}$=7.4 Hz, H-8), 1.33 (m, 4H, H-9, H-10), 0.90 (t, 3H, $^3J_{H,H}$=7.0, H-11). $^{13}$C NMR: δ 190.3, 153.2, 146.6, 117.2, 112.5, 38.9, 31.9, 24.4, 22.9, 14.3. DEP/CI/MS: m/z 167 [M+H]$^+$, Elemental Analysis: Calcd for C$_{10}$H$_{14}$O$_2$: C, 72.26; H, 8.49; O, 19.25. Found: C, 71.50; H, 8.70; O, 19.81.

EXAMPLE 3

Preparation of 2-Furyl-n-undecylketone (R=n-C$_{11}$H$_{23}$)—Magnesium turnings (21.6 g, 0.901 mol, 3.7 eq/halide) were covered with anhydrous Et$_2$O (150 mL) and a solution of 1-bromoundecane (54.0 mL, 0.242 mol) in anhydrous Et$_2$O (200 mL) was added in small aliquots until the reaction begins. The remaining bromoundecane solution was added dropwise, then heated to reflux (1 hour), allowed to cool to rt and then added to a cooled solution of the Weinreb amide (30.0 g, 0.194 mol in 200 mL anhydrous Et$_2$O, 0° C.) via cannula. The resulting slurry was stirred (3 h) and then quenched with equal amounts of 1 N HCl and H$_2$O. After warming to rt the mixture was separated and the aqueous layer was extracted with Et$_2$O (2×). The combined organics were washed with sat'd. NaHCO$_3$, brine, dried (Na$_2$SO$_4$), filtered, and evaporated to yield crude furyl ketone, which was distilled under vacuum (b.p. 131–138° C., 0.2 mm Hg) to give pure furyl ketone (40.2 g, 0.161 mol, Yld. 82.8%). $^1$H NMR: δ 7.55 (m, 1H, H-2), 7.15 (d, 1H, $^3J_{H,H}$=3.6 Hz, H-4), 6.50 (dd, 1H, $^3J_{H,H}$=1.7 Hz, $^3J_{H,H}$=3.6 Hz, H-3), 2.78 (t, 2H, $^3J_{H,H}$=7.5 Hz, H-7), 1.69 (quintet, 2H, $^3J_{H,H}$=7.4 Hz, H-8), 1.34–1.23 (m, 16H), 0.90 (t, 3H, $^3J_{H,H}$=7.1, CH$_3$). $^{13}$C NMR: δ 190.1, 153.3, 146.5, 117.1, 112.5, 38.9, 32.3, 30.1, 30.0, 29.9, 29.8, 29.7, 24.7, 23.0, 14.5.

EXAMPLE 4

Preparation of 1-(2-Furyl)-7-hydroxy-1-heptanone (R=n-C$_6$H$_{12}$OH)—Magnesium turnings (8.20 g, 0.342 mol, 4.5 eq/halide) were covered with anhydrous THF (40 mL) and a solution of 1-(tetrahydropyran-2-yloxy)-6-hexyl bromide (20.1 g, 76.0 mmol in anhydrous 100 mL THF) was added dropwise once the reaction was initiated with 1,2-dibromoethane. The remaining halide solution was added dropwise and the mixture was allowed to stir at rt overnight. The resulting mixture was then added to a cooled solution of the Weinreb amide (10.3 g, 66.1 mmol in 100 mL anhydrous THF, 0° C.) via cannula. The resulting slurry was stirred (3 h) and then quenched with equal amounts of 1 N HCl and H$_2$O. After warming to rt the mixture was separated and the aqueous layer was extracted with Et$_2$O (2×). The combined organics were washed with sat'd. NaHCO$_3$, brine, dried (Na$_2$SO$_4$), filtered, and evaporated to yield crude residue, which was then dissolved in MeOH (200 mL) with a small amount of TsOH and allowed to stir overnight. The reaction mixture was stirred with NaHCO$_3$, evaporated, and the residue taken up in hexane. The hexane portion was washed with H$_2$O (2×), brine, dried (Na$_2$SO$_4$), and concentrated to yield crude furyl ketone, which was distilled under vacuum (b.p. 164–167° C., 0.2 mm Hg) to give pure furyl ketone (6.95 g, 35.4 mmol, Yld. 53.6%). $^1$H NMR: δ 7.57 (dd, 1H, $^3J_{H,H}$=1.7 Hz, $^4J_{H,H}$=0.74 Hz, H-2), 7.17 (dd, 1H, $^3J_{H,H}$=3.6 Hz, $^4J_{H,H}$=0.76 Hz, H-4), 6.52 (dd, 1H, $^3J_{H,H}$=3.6 Hz, $^3J_{H,H}$=1.7 Hz, H-3), 3.63 (t, 2H, $^3J_{H,H}$=6.6 Hz, H-12), 2.81 (t, 2H, $^3J_{H,H}$=7.6 Hz, H-7), 2.13 (bs, 1H, OH), 1.72 (quintet, 2H, $^3J_{H,H}$=7.4 Hz, H-8), 1.57 (quintet, 2H, $^3J_{H,H}$=6.7 Hz, H-11), 1.39 (m, 4H, H-9 and 10). $^{13}$C NMR: δ 189.8, 152.7, 146.3, 117.0, 112.2, 62.8, 38.3, 32.5, 29.0, 25.5, 24.2.

EXAMPLE 5

Preparation of 2-Furyl-n-undecenylketone (R=n-C$_9$H$_{18}$CH=CH$_2$)—Magnesium turnings (2.0 g, 83.3 mmol) were covered with anhydrous Et$_2$O (10 mL) and a solution of 1-bromoundecene (5.0 mL, 23.0 mmol) in anhydrous Et$_2$O (15 mL) was added in small aliquots until the reaction begins. The remaining halide solution was added dropwise, then heated to reflux (1 hour), allowed to cool to rt and then added to a cooled solution of the Weinreb amide (2.82 g, 18.2 mmol in 15 mL anhydrous Et$_2$O, 0° C.) via cannula. The resulting slurry was stirred (3 h) and then quenched with equal amounts of 1 N HCl and H$_2$O. After warming to rt the mixture was separated and the aqueous layer was extracted with Et$_2$O (2×). The combined organics were washed with sat'd. NaHCO$_3$, brine, dried (Na$_2$SO$_4$), filtered, and evaporated to yield crude furyl ketone. $^1$H NMR: δ 7.58 (dd, 1H, $^3J_{H,H}$=1.7 Hz, $^4J_{H,H}$=0.74 Hz, H-2), 7.18 (dd, 1H, $^3J_{H,H}$=3.6 Hz, $^4J_{H,H}$=0.74 Hz, H-4), 6.53 (dd, 1H, $^3J_{H,H}$=1.7 Hz, $^3J_{H,H}$=3.6 Hz, H-3), 5.82 (m, 1H), 5.00 (m, 1H, vinyl), 4.92 (m, 1H, vinyl), 2.82 (t, 2H, $^3J_{H,H}$=7.5 Hz, H-7), 2.04 (qd, 2H, $^3J_{H,H}$=7.5 Hz, H-15), 1.72 (quintet, 2H, $^3J_{H,H}$=7.5 Hz, H-8), 1.37–1.20 (m, 12H). $^{13}$C NMR: δ 189.9, 152.9, 146.2, 139.2, 116.8, 114.1, 112.1, 38.5, 33.8, 29.7, 29.4, 29.3, 29.2, 29.1, 28.9, 24.3.

Obviously, many modifications and variations of the present invention are possible in light of the above teachings. It is therefore to be understood that the claimed invention may be practiced otherwise than as specifically described.

What is claimed is:

1. A method of making a compound comprising:
    providing a furyl compound, the furyl compound being a 2-furoyl chloride or corresponding carboxylic acid, amide, ester, anhydride, or lactone;
    reacting the furyl compound with CH$_3$O(CH$_3$)NH.HCl to form an amide;
    reacting the amide with a C$_5$ to C$_{14}$ alkane Grignard reagent or a C$_5$ to C$_{14}$ alkyllithium to form a chelated intermediate; and
    reacting the chelated intermediate with an aqueous acid to form a (2-furyl)-alkylketone.

2. The method of claim 1, wherein the reacting to form an amide is performed using pyridine as a solvent.

3. The method of claim 1, wherein the reacting to form an amide is performed using trichloromethane as a solvent.

4. The method of claim 1, further comprising:
    extracting the (2-furyl)-alkylketone using a polar/non-polar solvent pair; and
    purifying the (2-furyl)-alkylketone from the non-polar solvent.

5. The method of claim 4, further comprising:
    purifying the (2-furyl)-alkylketone by distillation.

6. The method of claim 1, wherein the alkane Grignard reagent contains a C$_7$–C$_9$ alkane.

7. The method of claim 6, wherein the $C_7$–$C_9$ alkane is terminated with a protected hydroxyl or tertiary amine group.

8. The method of claim 1, wherein the furyl compound is a 2-furoyl chloride.

9. The method of claim 1, wherein the alkyl group of the alkane Grignard reagent or alkyllithium is n-pentyl.

* * * * *